United States Patent
Al-Humydi et al.

(10) Patent No.: US 9,000,200 B2
(45) Date of Patent: Apr. 7, 2015

(54) PROCESS FOR THE PREPARATION OF METALLOCENE COMPLEXES

(71) Applicant: Saudi Basic Industries Corporation, Riyadh (SA)

(72) Inventors: Abdulaziz Hamad Al-Humydi, Riyadh (SA); Atieh Aburaqabah, Riyadh (SA); Christian Gorl, Bayreuth (DE); Helmut Alt, Bayreuth (DE)

(73) Assignee: Saudi Basic Industries Corporation, Riyadh (SA)

( * ) Notice: Subject to any disclaimer, the term of this patent is extended or adjusted under 35 U.S.C. 154(b) by 0 days.

(21) Appl. No.: 14/366,691

(22) PCT Filed: Dec. 13, 2012

(86) PCT No.: PCT/EP2012/005232
§ 371 (c)(1),
(2) Date: Jun. 19, 2014

(87) PCT Pub. No.: WO2013/091837
PCT Pub. Date: Jun. 27, 2013

(65) Prior Publication Data
US 2014/0378694 A1    Dec. 25, 2014

(30) Foreign Application Priority Data
Dec. 19, 2011 (EP) .................................... 11009974

(51) Int. Cl.
| C07C 1/32 | (2006.01) |
| C07F 17/00 | (2006.01) |
| C07F 7/00 | (2006.01) |
| C08F 110/02 | (2006.01) |
| C08F 4/659 | (2006.01) |

(52) U.S. Cl.
CPC . *C07F 7/00* (2013.01); *C07F 17/00* (2013.01); *C07C 1/321* (2013.01); *C07C 2102/08* (2013.01); *C08F 110/02* (2013.01); *C08F 4/65912* (2013.01)

(58) Field of Classification Search
CPC ........ C07F 17/00; C07F 7/00; C08F 4/65912; C08F 110/02; C07C 1/321; C07C 2102/08
USPC ........................................... 556/53; 585/469
See application file for complete search history.

(56) References Cited

U.S. PATENT DOCUMENTS
6,342,622 B1    1/2002    Arts et al.

FOREIGN PATENT DOCUMENTS
| EP | 1059300 A1 | 12/2000 |
| WO | 2013091836 A1 | 6/2013 |

OTHER PUBLICATIONS

Dong-won Lee et al., "A Convenient Approach to 2-Arylindenes via Suzuki Coupling Reaction of 2-Indenylboronate with Aryl Bromides", Bull. Korean Chem. Soc. 2004, vol. 25, No. 1, 29-30.
Ellis et al., "Synthesis, Structure, and Properties of Chiral Titanium and Zirconium Complexes Bearing Biaryl Strapped Substituted Cyclopentadienyl Ligands", Organometallics, 1993, 12, 4391-4401.
International Search Report and Written Opinion of the the International Searching Authority; International Application No. PCT/EP2012/005231; International Filing Date Dec. 13, 2012; 15 pages.
International Search Report; International Application No. PCT/EP2012/005232; Date of Mailing of International Search Report Feb. 14, 2013; 3 pages.
IJpeij et al., "A Suzuki Coupling Based Route to 2,2'-Bis(2-indenyl)biphenyl Derivatives", J. Org. Chem. 2002, 67, 169-176.
Liang et al., Palladium-Catalyzed Synthesis of Benzosilolo[2,3-b]indoles via Cleavage of a C(sp3)-Si Bond and Consquent Intramolecular C(sp2)-Si Coupling, J. Am. Chem. Soc. 2011, 133, 9204-9207.
Organic Chemistry, G. Marc Loudon, editor. 1984; 1(): 51-54.GN.

*Primary Examiner* — Porfirio Nazario Gonzalez
(74) *Attorney, Agent, or Firm* — Cantor Colburn LLP

(57) ABSTRACT

A process to prepared bridged bis(indenyl)ligands, comprising the step of reacting a 2-indenylpinacolyl borane compound with a bromosubstituted compound in the presence of a Pd catalyst and a base to form the corresponding bridged bis(indenyl) ligand. The process may further comprise the step of reacting a 2-bromo indene compound with pinacolborane in the presence of a Pd catalyst and a base to form the corresponding 2-indenylpinacolylborane compound. These bridged bis(indenyl)ligands may suitably be used in the preparation of metallocene complexes, such as 2,2'-bis(2-indenyl)biphenyl $ZrCl_2$ and 1,2-bis(2-indenyl)benzene $ZrCl_2$. These metallocene complexes may be used for the polymerization, optionally in the presence of a cocatalyst, of one or more α-olefins, preferably for the polymerization of ethylene.

12 Claims, No Drawings

PROCESS FOR THE PREPARATION OF METALLOCENE COMPLEXES

CROSS-REFERENCE TO RELATED APPLICATIONS

This application is a National Stage filing of PCT/EP20112/005232, filed Dec. 13, 2012, which claims priority to EP 11009974.4, filed Dec. 19, 2011, both of which are incorporated by reference herein in their entirety.

BACKGROUND

The invention relates to a process for the preparation of metallocene complexes, in particular the invention relates to a process for the preparation of bridged bis(indenyl)ligands that can be used for the preparation of metallocene complexes, to a metallocene complex obtained or obtainable by said process and to the use of the metallocene complexes thus obtained or obtainable in polyolefin polymerization.

Metallocene complexes with bridged bis(indenyl) ligands have proven to be highly active in the polymerization of α-olefins, such as ethylene after activation with aluminoxane cocatalysts. However, the known syntheses of the ligands used in the synthesis of these metallocene complexes are tedious as they include unstable intermediates and/or require commercially unattractive compounds. Therefore, there is a desire for synthetic routes that make these valuable metallocene complexes easily accessible.

E. G. Ijpeij et al., "A Suzuki coupling based route to 2,2'-bis(2-indenyl)biphenyl derivatives," *J. Org. Chem.*, 2002, 67, 167 describe a number of processes for the preparation of bridged bis(indenyl) ligands. Many of these rational pathways were not successful and only one reaction leads to the desired ligand precursor 2,2'-bis(2-indenyl)biphenyl. However, the yield of this route obtained by Ijpeij, E. G., et al. for only the last step was only 79%.

SUMMARY

It is the object of the invention to provide an improved process for the preparation of bridged bis(indenyl)ligands. It is another object of the invention to provide an improved process for the preparation of metallocene complexes with bridged bis(indenyl) ligands.

This object is achieved by a process comprising the step of reacting a 2-indenylpinacolylborane compound of formula (1)

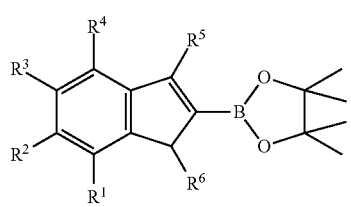

wherein $R^1$, $R^2$, $R^3$, $R^4$, $R^5$, $R^6$ each independently stand for H, a hydrocarbon radical having 1-20 C-atoms, a halide, an alkoxy group having 1-6 C-atoms, an alkylsulphide, an amine, a Si or B containing group or a P-containing group with a bromosubstituted compound of formula (2)

wherein R stands for a bridging group containing at least two sp2-hybridised carbon atoms that are bonded to the indenyl groups at the 2-positions in a solvent in the presence of a Pd catalyst and a base to form the corresponding bridged bis (indenyl) ligand of formula (3)

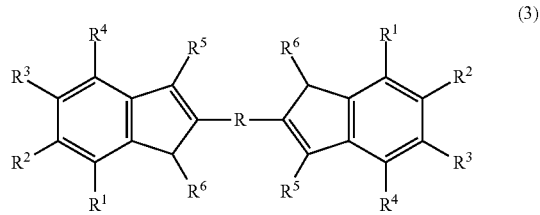

wherein R and $R^1$, $R^2$, $R^3$, $R^4$, $R^5$ are $R^6$ as described above.

DETAILED DESCRIPTION

It has surprisingly been found that the process of the invention leads to less (homo-coupled) byproducts that are laborious to separate from the desired ligand of formula (3). A good yield can thus be obtained using the process of the invention.

The Pd catalysts that can be used in the preparation of the bridged bis(indenyl) ligand of formula (3) are in principle all Pd catalysts known to be suitable for Suzuki couplings.

Preferably, a Pd(0) catalyst or a catalyst wherein Pd(0) is generated in situ by reduction of (more stable) Pd(II) compounds is used. Examples of Pd catalysts include tetrakis (triphenylphosphin)palladium (($Ph_3P)_4Pd$), palladium (II) acetate ($Pd(O_2CCH_3)_2$ or $Pd(Oac)_2$), tris(dibenzylideneacetone)dipalladium ($PD(dba)_2$) and bis(triphenylphosphin) palladium dichloride (($PPh_3)_2PdCl_2$)

Preferably as Pd catalyst, bis(triphenylphosphin)palladium dichloride (($PPh_3)_2PdCl_2$) is used, since—besides the fact that this catalyst leads to a good yield, the catalyst is also commercially attractive.

The base that can be used in the preparation of the bridged bis-(indenyl) ligand of formula (3) can in principle be any base, for example an inorganic or an organic base. Preferably an organic base is used in the preparation of the bridged bis-indenyl) ligand of formula (3), such as for example a quaternary ammonium salt, for example tetra n-butylammoniumacetate or a tertiary amine, for example triethylamine ($Et_3N$). Other examples of suitable based include but are not limited to sodium tert-butoxide, potassium carbonate, lithium hydroxide, sodium hydroxide, sodium ethoxide, potassium fluoride and potassium phosphate.

The process to form the bridged bis-(indenyl) ligand of formula (3) as described above may in principle be performed in any solvent known to be suitable for Suzuki couplings. alcohols, for example methanol or ethanol; aromatic solvents, for example benzene, toluene or xylene; ethers, for example tetrahydrofuran, dioxane or dimethoxyethane; amides, for example dimethylformamide. Preferably organic solvents are used, more preferably ethers, more preferably dioxane. Mixtures of solvents, such as the solvents mentioned herein may also be used.

In principle, the reaction conditions for the process to form the bridged bis-indenyl) ligand of formula (3) are not critical and the temperatures, pressures and reaction time known to be suitable for Suzuki couplings, may be used by the person skilled in the art and optimal conditions can be found using routine experimentation. For example, the temperature may be from 60 to 120° C., as at temperatures below 60° C., the reaction hardly proceeds and at temperatures of above 120° C., tarring may occur. Preferably, the temperature is chosen to be at least 60, preferably at least 75 and/or at most 100, preferably at most 85° C. The pressure under which the process is performed is preferably atmospheric pressure (1 bar). The reaction time may for example be in the range from 36 to 48 hours.

R stands for a bridging group containing at least two sp2-hybridised carbon atoms that are bonded to the indenyl groups at the 2-positions.

In general and in this description, the substituent locants of the indenyl ring are numbered in accordance with the IUPAC Nomenclature of Organic Chemistry, 1979, rule A 21.1. The numbering of the substituents for indene is given below in formula (7). This numbering is analogous in the case of an indenyl ligand:

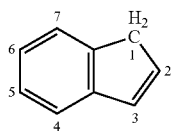

(7)

The R group connects the two indenyl groups in the bridged bis(indenyl) ligand of formula (3). Sp2-hybridised carbon atoms are also known as trigonal carbon atoms. The chemistry related to sp2-hybridised carbon atoms is for instance described by S. N. Ege, Organic Chemistry, D.C. Heath and Co., 1984, p. 51-54. Sp2-hybridised carbon atoms are carbon atoms that are connected to three other atoms. In the bridged bis(indenyl) ligand of formula (3), the sp2-hybridised carbon atoms are in any case connected to the indenyl groups at the 2-position.

The sp2-hybridised carbon atom may be a part of, for instance, an alkylene containing bridging group R or of an aryl containing bridging group R.

Examples of alkylene-containing bridging groups include but are not limited to optionally substituted ethylene and propylene.

Examples of aryl group containing bridging groups R include but are not limited to phenylene, biphenylene, pyridyl, furyl, thiophyl and N-substituted pyrroles, such as N-phenylpyrrole or an inorganic compound containing an aromatic group, for instance a metallocene compound or a ferrocene compound.

The bridging group R preferably contains at least one aryl group; for example the aryl group may be a monoaryl group, for example phenylene or naphthalene or a biaryl group, for example biphenylidene or binaphthyl. Preferably the bridging group R stands for an aryl group, preferably R stands for a phenylene or biphenylidene group.

The bridging group R may be connected to the indenyl groups via any sp2 hybridised carbon atom, for example a phenylene group may be connected via the 1 and the 2 position, a biphenylene group may be connected via the 2 and 2'-position, a naphthalene group may be connected via the 2 and 3-position, a binapthyl group may be connected via the 2 and 2'-position. Preferably R stands for a phenylene group that is connected to the indenyl groups via the 1 and the 2 position (the compound of formula (3) is 1,2-bis(2-indenyl)benzene in case $R^1$, $R^2$, $R^3$, $R^4$, $R^5$ and $R^6$ all stand for H) or R stands for a biphenylene group that is connected via the 2 and 2'-position (the compound of formula (3) is 2,2'-bis(2-indenyl)biphenyl in case $R^1$, $R^2$, $R^3$, $R^4$, $R^5$ and $R^6$ all stand for H).

Compounds of formula (2):

(2), wherein R is as defined herein are commercially available and/or can easily be synthesized using methods known in the art (for instance as described in the Journal of the America Chemical Society, 133 (24), 9204-9207; 2011). For example 2,2'-dibromobiphenyl (R stands for a biphenyl) may be prepared by reaction of 1,2-dibromobenzene with n-butyl-lithium (n-BuLi) in a molar ratio of 2 mol 1,2-dibromobenzene to 1 mol n-butyl-lithium at a temperature well below 0° C., for example at a temperature below −40° C., for example at a temperature of about −65° C. in an organic solvent, for example in tetrahydrofuran and/or n-hexane. The process of the invention avoids the use of very unstable dilithio compounds.

$R^1$, $R^2$, $R^3$, $R^4$, $R^5$ and $R^6$ may each independently stand for H, a hydrocarbon radical having 1-20 C-atoms, a halide, an alkoxy group having 1-6 C-atoms, an alkylsulphide, an amine, a Si or B containing group or a P-containing group, preferably for H, a hydrocarbon radical having 1-20 C-atoms or a halide. Examples of hydrocarbon radicals include alkyl groups, for example methyl, ethyl, propyl, butyl, hexyl and decyl; aryl groups, for example phenyl, mesityl, tolyl and cumenyl; aralkyl groups for example benzyl, pentamethylbenzyl, xylyl, styryl and trityl and alkaryl groups. The hydrocarbon radical preferably has from 1-6 C-atoms and is most preferably methyl. Examples of halides include chloride, bromide and fluoride. Examples of alkoxy groups having 1-6 C-atoms include but are not limited to methoxy, ethoxy and phenoxy. Examples of alkylsulphides include methylsulphide, phenylsulphide and n-butylsulphide. Examples of amines include dimethylamine, n-butylamine Examples of Si or B containing groups include trimethylsilicium ($Me_3Si$) and diethylboron ($Et_2B$). Examples of P-containing groups include dimethylphosphor ($Me_2P$) and diphenylphosphor ($Ph_2P$).

Preferably, $R^5$ and/or $R^6$ stand for H. More preferably, $R^1$ and/or $R^2$ and/or $R^3$ and/or $R^4$ and/or $R^5$ and/or $R^6$ stand for H. Most preferably $R^1$, $R^2$, $R^3$, $R^4$, $R^5$ and $R^6$ all stand for H.

The 2-indenylpinacolylborane compound of formula (1) wherein $R^1$, $R^2$, $R^3$, $R^4$, $R^5$ and $R^6$ are as defined herein may be prepared by reacting a 2-bromo indene compound of formula (4)

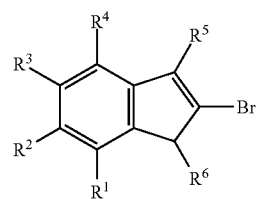

(4)

with pinacolborane (represented by formula (5))

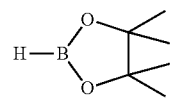

(5)

in the presence of a Pd catalyst and a base to form the corresponding 2-indenylpinacolylborane compound of formula (1).

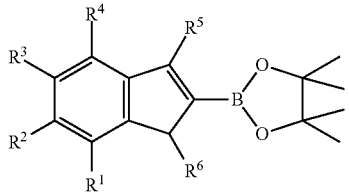
(1)

By using the widely available 2-bromo indene compound of formula (4), the corresponding fairly stable 2-indenylpinacolylborane compound of formula (1) can be prepared.

The 2-indenylpinacolylborane of formula (1) can be used as an intermediate for the preparation of a bridged bis(indenyl)ligand. The invention thus also provides an easy two-step process for the preparation of a bridged bis(indenyl) ligand of formula (3).

In a special embodiment, therefore, the invention relates to a process according to the invention further comprising the step of reacting a 2-bromo indene compound of formula (4)

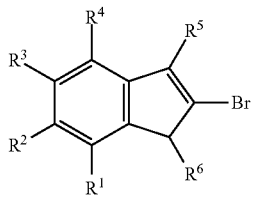
(4)

with pinacolborane (represented by formula (5))

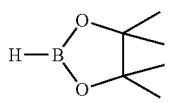
(5)

in the presence of a Pd catalyst and a base to form the corresponding 2-indenylpinacolylborane compound of formula (1)

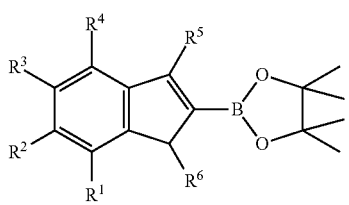
(1)

wherein $R^1$, $R^2$, $R^3$, $R^4$, $R^5$ and $R^6$ are as defined herein.

The invention also relates to a process comprising the steps of reacting a 2-bromo indene compound of formula (4)

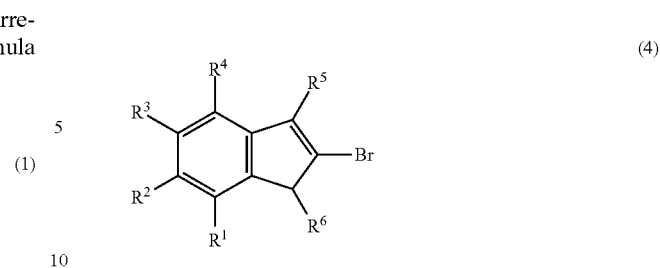
(4)

with pinacolborane (represented by formula (5))

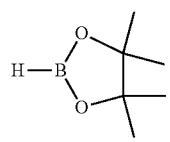
(5)

in a solvent in the presence of a Pd catalyst and a base to form the corresponding 2-indenylpinacolylborane compound of formula (1) and reacting the 2-indenylpinacolylborane compound of formula (1)

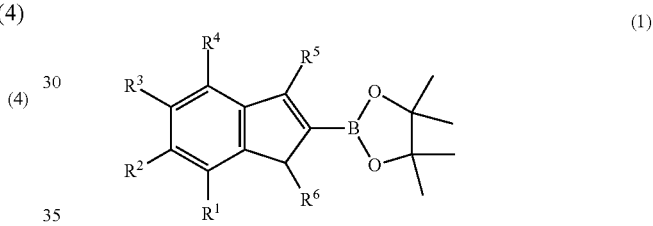
(1)

wherein $R^1$, $R^2$, $R^3$, $R^4$, $R^5$, $R^6$ each independently stand for H, a hydrocarbon radical having 1-20 C-atoms, a halide, an alkoxy group having 1-6 C-atoms, an alkylsulphide, an amine, a Si or B containing group or a P-containing group with a bromosubstituted compound of formula (2)

$$(Br)_2—R \qquad (2)$$

wherein R stands for a bridging group containing at least two sp2-hybridised carbon atoms that are bonded to the indenyl groups at the 2-positions
in the presence of a Pd catalyst and a base to form the corresponding bridged bis(indenyl) ligand of formula (3)

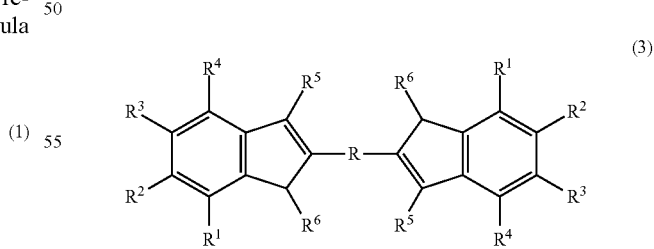
(3)

wherein R, $R^1$, $R^2$, $R^3$, $R^4$, $R^5$ and $R^6$ are as described herein.

The Pd catalysts that can be used in the preparation of the 2-indenylpinacolylborane compound of formula (1) are in principle all Pd catalysts known to be suitable for transition metal mediated coupling procedures such as for example Heck, Sonogashira or Suzuki couplings. Preferably, a Pd(0) catalyst or a catalyst wherein Pd(0) is generated in situ by reduction of (more stable) Pd(II) compounds is used. Examples of Pd catalysts include tetrakis(triphenylphosphin) palladium ((Ph$_3$P)$_4$Pd) and bis(triphenylphosphin)palladium dichloride (PPh$_3$)$_2$PdCl$_2$).

Preferably as Pd catalyst, bis(triphenylphosphin)palladium dichloride (PPh$_3$)$_2$PdCl$_2$) is used.

By using the cost-effective Pd catalyst bis(triphenylphosphin)palladium dichloride both for the preparation of the bridged bis(indenyl)ligand of formula (3) and for the preparation of the 2-indenylpinacolylborane compound of formula (1), the two-step process for the preparation of a bridged bis(indenyl) ligand has a good yield and is also very commercially attractive.

The base that can be used in the preparation of the 2-indenylpinacolylborane compound of formula (1) can in principle be any base, for example an inorganic or an organic base. Preferably an inorganic base is used in the preparation of the 2-indenylpinacolylborane compound of formula (1). An example of an inorganic base includes but is not limited to K$_3$PO$_4$.

The process to form the 2-indenylpinacolylborane compound of formula (1) as described above may in principle be performed in any solvent known to be suitable for transition metal mediated coupling procedures, such as for example Heck, Sonogashira or Suzuki couplings. Examples of solvents for said process include organic solvents such as tetrahydrofuran (THF).

In principle, the reaction conditions for the process to form the 2-indenylpinacolyl borane compound of formula (1) are not critical and the temperatures, pressures and reaction time known to be suitable for transition metal mediated coupling procedures, such as for example Heck, Sonogashira or Suzuki couplings, may be used by the person skilled in the art and optimal conditions can be found using routine experimentation. For example, the temperature may be from 60 to 120° C., as at temperatures below 60° C., the reaction hardly proceeds and at temperatures of above 120° C., tarring may occur. Preferably, the temperature is chosen to be at least 60, preferably at least 75 and/or at most 100, preferably at most 85° C. The pressure under which the process is performed is preferably atmospheric pressure (1 bar). The reaction time may for example be in the range from 36 to 48 hours.

The bridged bis(indenyl) ligand of formula (3) may be further converted into a metallocene complex of formula (6)

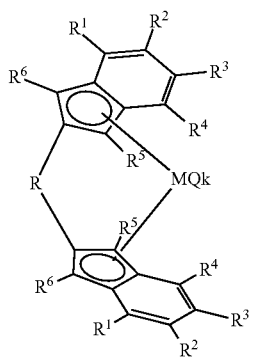

(6)

wherein M stands for a transition metal from the group of lanthanides or from group 3, 4, 5 or 6 of the Periodic System of Elements, wherein Q stands for an anionic ligand to M, wherein k is an integer and represents the number of anionic ligands, and wherein R, R$^1$, R$^2$, R$^3$, R$^4$, R$^5$ and R$^6$ are as described herein according to a process known per se.

For example, a metallocene complex of formula (6) may be prepared in a two-step procedure as for example described in EP1059300A1, hereby incorporated by reference. Specifically in paragraph [0036] of EP1059300A1, it is described that the bridged bis(indenyl) ligand of formula (3) may first be converted into its dianion using for example an organometallic compound, an amine, a metal hydride, an alkaline earth metal or an alkaline earth metal.

Organolithium, organomagnesium and organosodium compound may for example be used, but also sodium or potassium. Organolithium compounds, such as methyllithium or n-butyllithium are particularly suitable for converting the bridged bis(indenyl) ligand of formula (3) into its dianion.

In paragraph [0037] of EP1059300A1, it is described that the dianion corresponding to a bridged bis(indenyl) ligand may be converted into the corresponding metallocene complex by transmetalation with a compound of transition metal M, wherein M is as defined herein. See for example EP-A-420436 or EP-A-427697. The process described in NL-A-91011502 is particularly suitable. Examples of compounds of transition metal M include but are not limited to TiCl$_4$, ZrCl$_4$, HfCl$_4$, Zr(OBu)$_4$ and Zr(OBu)$_2$Cl$_2$. The transmetalation may be carried out as in NL-A-91011502 in a solvent or in a combination of solvents that weakly coordinate to transition metals from the groups 3, 4, 5, or 6 of the Periodic System of Elements with at most 1 mole equivalent, relative to the transition metal compound started from, of a Lewis base of which the conjugated acid has a pK$_a$ greater than −2.5. Examples of solvents/dispersants (pK$_a$ of conjugated acid=<−2.5) that may suitably be used in such transmetalation include but are not limited to ethoxyethane, dimethoxyethane, isopropoxyisopropane, n-propoxy-n-propane, methoxybenzene, methoxymethane, n-butoxy-n-butane, ethoxy-n-butane and dioxane. Part of the reaction medium used for the transmetalation may consist of hydrocarbons (hexane and the like).

Therefore, the invention also relates to the process of the invention further comprising the step of converting the bridged bis(indenyl)ligand of formula (3) into the corresponding metallocene complexes of formula (6)

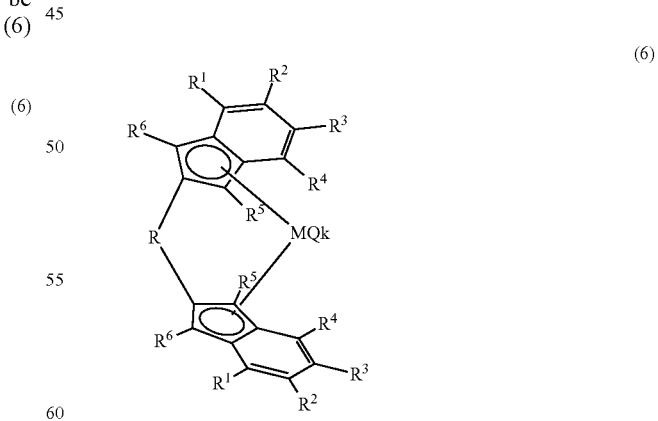

(6)

wherein M stands for a transition metal from the group of lanthanides or from group 3, 4, 5 or 6 of the Periodic System of Elements, wherein Q stands for an anionic ligand to M, wherein k is an integer and stands for the number of anionic ligands, and wherein R, R$^1$, R$^2$, R$^3$, R$^4$, R$^5$ and R$^6$ are as described herein according to a process known per se.

In particular, the invention also relates to a process of the invention further comprising the steps of converting the bridged bis(indenyl) ligand of formula (3) into its corresponding dianion using an organometallic compound, an amine, a metal hydride, an alkaline earth metal or an alkaline earth metal and transmetalating the formed dianion with a compound of transition metal M, wherein M is as defined herein to form the corresponding metallocene complex of formula (6)

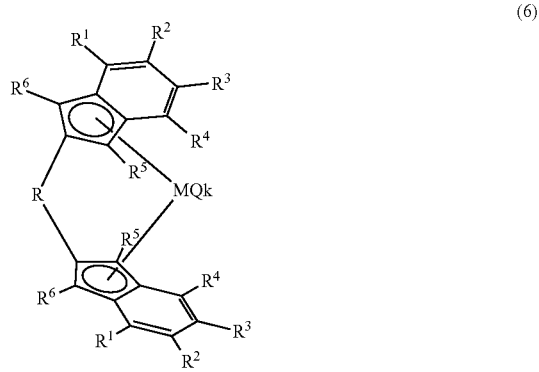

(6)

The transition metal M is selected from the lanthanides or from group 3, 4, 5 or 6 of the Periodic System of Elements. The Periodic System of Elements is understood to be the new IUPAC version as printed on the inside cover of the Handbook of Chemistry and Physics, 70th edition, CRC Press, 1989-1990.

Preferably, M stands for Ti, Zr, Hf, V or Sm, more preferably for Ti, Zr, Hf, more preferably for preferably for Zr or Hf, even more preferably for Zr. Complexes of formula (6), wherein M stands for Zr or Hf metallocene may suitably be used as catalysts in the synthesis of polyethylene or the synthesis of polypropylene. The expression 'synthesis/preparation of polyethylene' referred herein is defined as homopolymerization or copolymerization of ethylene with one or more α-olefins having 3-12 C-atoms and optionally one or more non-conjugated dienes.

Q stands for an anionic ligand to the transition metal M. The anionic ligand may comprise one or more uni- or polyvalent anionic ligands. Examples of such ligands include but are not limited to a hydrogen atom, a halogen atom, an alkyl group, an aryl group, an aralkyl group, an alkoxy group, an aryloxy group and a group with a heteroatom chosen from group 14, 15 or 16 of the Periodic System of Elements, such as for example an amine group or amide group; a sulphur containing group, for example sulphide or sulphite; a phosphorus containing group, for example phosphine or phosphite.

Q may also be a monoanionic ligand bonded to the transition metal M via a covalent metal-carbon bond and which is additionally capable to non-covalently interact with M via one of more functional groups. The functional group mentioned above can be one atom, but also a group of atoms connected together. The functional group is preferably an atom of group 17 of the Periodic Table of Elements or a group containing one or more elements from groups 15, 16 or 17 of the Periodic Table of Elements. Examples of functional groups are F, Cl, Br, dialkylamino and alkoxy groups.

Q may for example be a phenyl group in which at least one of the ortho-positions is substituted with a functional group capable of donating electron density to the transition metal M.

Q may also be a methyl group in which one or more of the alpha-positions is substituted with a functional group capable of donating electron density to the transition metal M. Examples of methyl groups substituted in one or more of the alpha-positions are benzyl, diphenylmethyl, ethyl, propyl and butyl substituted with a functional group capable of donating electron density to the transition metal M. Preferably at least one of the ortho-positions of a benzyl-group is substituted with a functional group capable of donating electron density to the transition metal M.

Examples of these Q groups include, but are not limited to: 2,6-difluorophenyl, 2,4,6-trifluorophenyl, pentafluorophenyl, 2-alkoxyphenyl, 2,6-dialkoxyphenyl, 2,4,6-tri(trifluoromethyl)phenyl, 2,6-di(trifluoromethyl)phenyl, 2-trifluoromethylphenyl, 2-(dialkylamino)benzyl and 2,6-(dialkylamino)phenyl.

Q may for example stand for a mono-anionic ligand, for example for methyl of Cl, preferably for Cl.

The number of Q groups in the metallocene complex of formula (6) (represented by the integer k in formula (6)) is determined by the valence of the transition metal M and the valence of the Q groups. In the metallocene complex of formula (6), k is equal to the valence of M minus 2 divided by the valence of Q. For example, in case M stands for Zr and Q stands for Cl, k is 2.

The metallocene complex of formula (6) may be used, optionally in the presence of a cocatalyst for the polymerization of one or more α-olefins, preferably for the polymerization of ethylene, for example in solution or suspension polymerization of ethylene.

The α-olefin(s) is/are preferably chosen from the group comprising ethylene, propylene, butene, pentene, hexene, heptene and octene, while mixtures can also be used. More preferably, ethylene and/or propylene is/are used as α-olefin. The use of such α-olefins leads to the formation of crystalline polyethylene homopolymers and copolymers of both low and high density (HDPE, LDPE, LLDPE, etc.), and polypropylene homopolymers and copolymers (PP and EMPP). The monomers needed for such products and the processes to be used are known to the skilled in the art.

The metallocene complex of formula (6) is also suitable for the preparation of amorphous or rubbery copolymers based on ethylene and another α-olefin. Propylene is preferably used as the other α-olefin, so that EPM rubber is formed.

Details of such use and examples of cocatalysts may be found in EP 1059300 A1, paragraphs [0038]-[0057], hereby incorporated by reference.

According to a preferred embodiment of the invention the metallocene complex according to the invention is used in the preparation of LLDPE in a gas phase polymerisation.

The cocatalyst for the polymerization of one or more α-olefins can be an organometallic compound. The metal of the organometallic compound can be selected from group 1, 2, 12 or 13 of the Periodic Table of Elements. Suitable metals include sodium, lithium, zinc, magnesium, and aluminium, preferably aluminium. At least one hydrocarbon radical is bonded directly to the metal to provide a carbon-metal bond. The hydrocarbon group used in such compounds preferably contains 1-30, more preferably 1-10 carbon atoms. Examples of suitable compounds include, amyl sodium, butyl lithium, diethyl zinc, butyl magnesium chloride, and dibutyl magnesium. Preference is given to organoaluminium compounds, including, for example and without limitation, the following: trialkyl aluminium compounds, such as triethyl aluminium and tri-isobutyl aluminium; alkyl aluminium hydrides, such as diisobutyl aluminium hydride; alkylalkoxy organoaluminium compounds; and halogen-containing organoaluminium compounds, such as diethyl aluminium chloride, diisobutyl aluminium chloride, and ethyl aluminium sesquichloride. Preferably, aluminoxanes are selected as the organoaluminium compound.

The aluminoxanes can also be aluminoxanes containing a low amount of trialkylaluminium; preferably 0.5 to 15 mol % trialkylaluminium. In this case the amount of trialkylaluminium is more preferably 1-12 mol % trialkylaluminium.

In addition or as an alternative to the organometallic compounds as the cocatalyst, the polymerization may be performed in the presence of a compound which contains or yields in a reaction with the metallocene complex of formula (6), a non-coordinating or poorly coordinating anion. Such compounds have been described for instance in EP-A-426,637, the complete disclosure of which is incorporated herein by reference. Such an anion is bonded sufficiently unstably such that it is replaced by an unsaturated monomer during the copolymerization. Such compounds are also mentioned in EP-A-277,003 and EP-A-277,004, the complete disclosures of which are incorporated herein by reference. Such a compound preferably contains a triaryl borane or a tetraaryl borate or an aluminium or silicon equivalent thereof Examples of suitable cocatalyst compounds include, without limitation, the following:

dimethyl anilinium tetrakis(pentafluorophenyl)borate $[C_6H_5N(CH_3)_2H]^+[B(C_6F_5)_4]^-$;

dimethyl anilinium bis(7,8-dicarbaundecaborate)-cobaltate (III);

tri(n-butyl)ammonium tetraphenyl borate;

triphenylcarbenium tetrakis(pentafluorophenyl)borate;

dimethylanilinium tetraphenyl borate;

tris(pentafluorophenyl)borane; and tetrakis(pentafluorophenyl)borate.

As described for instance in EP-A-500,944, the complete disclosure of which is incorporated herein by reference, the reaction product of a halogenated transition metal complex and an organometallic compound, such as for instance triethyl aluminium (TEA), can also be used.

The molar ratio of the cocatalyst relative to the transition metal complex (metallocene complex of formula (6)), in case an organometallic compound is selected as the cocatalyst, usually is in a range of from about 1:1 to about 10,000:1, and preferably is in a range of from about 1:1 to about 2,500:1. If a compound containing or yielding a non-coordinating or poorly coordinating anion is selected as cocatalyst, the molar ratio usually is in a range of from about 1:100 to about 1,000:1, and preferably is in a range of from about 1:2 to about 250:1.

The metallocene complex of formula (6) as well as the cocatalyst may be used in the polymerizations of α-olefins as a single component or as a mixture of several components. As is known to the person skilled in the art, a mixture may for instance be desired where there is a need to influence the molecular properties of the polymer, such as molecular weight and in particular molecular weight distribution.

The metallocene complex of formula (6) can be used supported as well as non-supported. The supported catalysts are used mainly in gas phase and slurry processes. The carrier used may be any carrier known as carrier material for catalysts, for instance silica, alumina or $MgCl_2$. Preferably, the carrier material is silica.

Polymerization of α-olefins can be effected in a known manner, in the gas phase as well as in a liquid reaction medium. In the latter case, both solution and suspension polymerization are suitable, while the quantity of transition metal to be used generally is such that its concentration in the dispersion agent amounts to $10^{-8}$-$10^{-4}$ mol/l, preferably $10^{-7}$-$10^{-3}$ mol/l.

The polymerizations using the metallocene complex of formula (6) will hereafter be explained in further detail with reference to a polyethylene preparation known per se, which is representative of the α-olefin polymerizations meant here. For the preparation of other polymers on the basis of an α-olefin, the reader is expressly referred to the multitude of publications on this subject.

The preparation (polymerization) of polyethylene referred to herein is defined as homopolymerization or copolymerization of ethylene with one or more α-olefins having 3-12 carbon atoms and optionally one or more non-conjugated dienes. The α-olefins that are particularly suitable include propylene, butene, hexene and octene. Suitable dienes include for instance 1,7-octadiene and 1,9-decadiene.

Any liquid that is inert relative to the catalyst system (the metallocene complex of formula (6) and the optional cocatalyst) may be used as dispersion agent in the polymerization. One or more saturated, straight or branched aliphatic hydrocarbons, such as butanes, pentanes, hexanes, heptanes, pentamethyl heptane or mineral oil fractions such as light or regular petrol, naphtha, kerosine or gas oil are suitable for that purpose. Aromatic hydrocarbons, for instance benzene and toluene, can be used, but because of their cost as well as on account of safety considerations, it will be preferred not to use such solvents for production on a technical scale. In polymerization processes on a technical scale, it is preferred therefore to use as solvent the low-priced aliphatic hydrocarbons or mixtures thereof, as marketed by the petrochemical industry. If an aliphatic hydrocarbon is used as solvent, the solvent may yet contain minor quantities of aromatic hydrocarbon, for instance toluene. Thus, if for instance methyl aluminoxane (MAO) is used as cocatalyst, toluene can be used as solvent in order to supply the MAO in dissolved form to the polymerization reactor. Drying or purification is desirable if such solvents are used; this can be done without problems by the average person skilled in the art.

A solution polymerization is preferably carried out at temperatures between 150° C. and 250° C.; in general, a suspension polymerization takes place at lower temperatures, preferably below 100° C.

The polymer solution resulting from the polymerization can be worked up by a method known per se. In general the catalyst system is de-activated at some point during the processing of the polymer. The deactivation is also effected in a manner known per se, e.g. by means of water or an alcohol. Removal of the catalyst system residues can usually be omitted when the quantity of metallocene complex of formula (6) in the polymer, in particular the content of halogen and transition metal is very low.

Polymerization can be effected at atmospheric pressure, but also at an elevated pressure of up to 500 MPa, continuously or discontinuously. If the polymerization is carried out under pressure, the yield of polymer can be increased additionally, resulting in an even lower catalyst residue content. Preferably, the polymerization is performed at pressures between 0.1 and 25 MPa. Higher pressures, of 100 MPa and upwards, can be applied if the polymerization is carried out in so-called high-pressure reactors. In such a high-pressure process the metallocene complex of formula (6) can also be used with good results.

The polymerization can also be performed in several steps, in series as well as in parallel. If required, the catalyst composition, temperature, hydrogen concentration, pressure, residence time, etc. may be varied from step to step. In this way it is also possible to obtain products with a wide molecular weight distribution.

The process of the invention leads to metallocene complexes of formula (6) in a higher purity and with less byproducts. These metallocene complexes of formula (6) thus obtained have a higher activity than the known complexes (production polyethylene in kg per mol complex of formula (6) per hour). Therefore, the invention also relates to a metallocene complex of formula (6) obtainable by the process of the invention. Also, the invention relates to a composition comprising the metallocene complex of formula (6) obtained or obtainable by the process of the invention.

In another embodiment, the invention relates to a metallocene complex of formula (6) which has an activity of at least 95,000 kg polyethylene (PE) produced per mol catalyst per hour as determined using the following conditions: Al/Zr=2500, 250 ml n-pentane, 10 bar ethylene, 60° C., 1 h. The invention also relates to a composition comprising the metallocene complex of formula (6), which has an activity of at least 95,000 kg polyethylene (PE) produced per mol catalyst per hour as determined using the following conditions: Al/Zr=2500, 250 ml n-pentane, 10 bar ethylene, 60° C., 1 h. The polymerization activity was determined (kg polyethylene (PE) produced per mol catalyst per hour)

In another embodiment, the invention relates to the use of the metallocene complexes of formula (6) obtained or obtainable by the process of the invention for the polymerization, optionally in the presence of a cocatalyst, of one or more α-olefins, preferably ethylene, for example in solution or suspension polymerization of ethylene.

The invention also relates to the use of a composition comprising the metallocene complex of formula (6) obtained or obtainable by the process of the invention for polymerization, optionally in the presence of a cocatalyst, or one or more α-olefins, preferably ethylene, for example in solution or suspension polymerization of ethylene.

The invention is now further elucidated by way of the following examples, without however being limited thereto.

EXAMPLES

1. Synthesis of 2,2'-bis(2-indenyl)-biphenyl 1.1 Synthesis of 2,2'-Dibromobiphenyl The synthesis of 2,2'-dibromobiphenyl from 1,2-dibromobenzene is schematically represented in reaction 1:

(reaction 1)

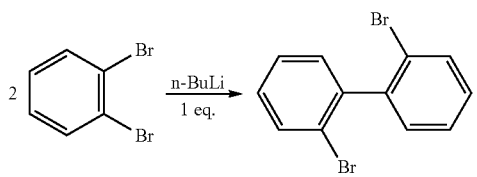

To a solution of 10.00 g (42.39 mmol) of o-dibromobenzene in 80 mL of THF, 8.5 mL of a 1.6 M solution of n-BuLi (21.2 mmol) in n-hexane was added dropwise, under an atmosphere of argon while the temperature was maintained below −65° C. After addition, the mixture was warmed to 0° C. and subsequently hydrolyzed with 100 mL of a 1 M HCl solution. The organic solvents were removed by rotary evaporation, and the residue was extracted with diethyl ether. The combined organic layers were washed (brine), dried (Na$_2$SO$_4$), filtered, and evaporated to dryness. The brown residue was crystallized from EtOH, yielding 3.96 g (58%) of a white solid (mp 78.8-79.2° C., lit. 27 80-81° C.) which was characterized by $^1$H NMR and $^{13}$C NMR spectroscopy and GC/MS as pure 2,2'-dibromobiphenyl: $^1$H NMR (CDCl$_3$, 200.1 MHz, reference CHCl$_3$ 7.27 ppm) 7.44 (m, 6H), 7.66-7.71 (m, 2H); GC/MS m/z (relative intensity) 310 (M$^+$, C$_{12}$H$_8$$^{79}$Br$_2$, 25), 231 (C$_{12}$H$_8$Br$^+$, 64), 152, (C$_{12}$H$_8$$^+$, 100).

1.2 Synthesis of 2-indenylboronate

The synthesis of 2-indenylboronate (2-indenylpinacolylborane) from 2-bromoindene and pinacolborane is schematically represented by reaction 2 below:

(reaction 2)

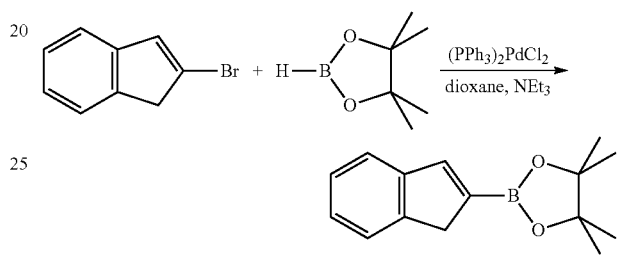

(PPh$_3$)$_2$PdCl$_2$ (0.54 g, 0.77 mmol) and 2-bromoindene (4.98 g, 25.54 mmol) were placed in an oven-dried Schlenk flask and dioxane (50 mL) was added. Triethylamine (10.7 mL, 76.6 mmol) and 4,4,5,5-tetramethyl-1,3,2-dioxaborolane (5.56 mL, 38.31 mmol) were added successively by syringe at room temperature (25° C.) under nitrogen. The reaction flask was stirred at 80° C. for 5.5 h. The reaction mixture was cooled to room temperature and quenched with water, and saturated brine (20 mL) was added. The organic layer was separated and the aqueous layer was extracted with ethyl ether (2×50 mL). The combined organic layers were washed with brine, dried over Na$_2$SO$_4$ and concentrated. The residue was purified by Kugelrohr distillation to give 2-indenylboronate as a white solid (mp 73-74° C.) in 69% yield. The product can be stored and handled in air. $^1$H NMR (300 MHz, CDCl$_3$) 7.58 (s, 1H), 7.50 (d, J=7 Hz, 1H), 7.46 (d, J=7 Hz, 1H), 7.30-7.21 (m, 2H), 3.54 (s, 2H), 1.33 (s, 12H); $^{13}$C NMR (75 MHz, CDCl$_3$) 147.0, 145.7, 145.0, 126.3, 126.0, 124.0, 122.0, 83.6, 41.7, 25.1.

1.3 Coupling of 2,2'-dibromobiphenyl with 2-indenylboronate

The reaction of 2,2'-dibromobiphenyl with 2-indenylpinacolylborane (2-indenylboronate) to form the corresponding phenylidene bridged bis(indenyl)ligand is schematically represented by reaction 3 below:

(reaction 3)

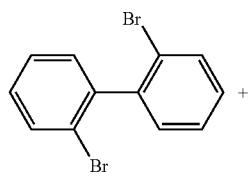

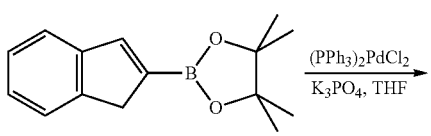

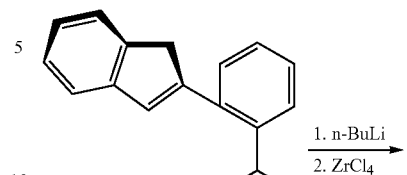

(reaction 4)

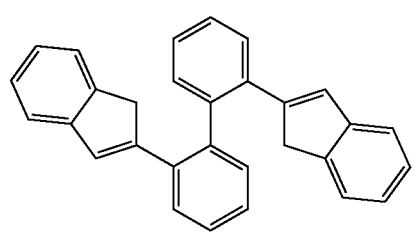

An oven-dried resealable Schlenk tube was charged with (PPh$_3$)$_2$PdCl$_2$ (26 mg; 0.037 mmol; 5 mol-% related to the boronate), 2-indenylboronate (0.18 g; 0.74 mmol) and K$_3$PO$_4$ (0.47 g; 2.23 mmol). The Schlenk tube was evacuated and backfilled with argon, and THF (10 ml) and 2,2'-dibromobiphenyl (0.115 g; 0.37 mmol) were added. The Schlenk tube was sealed and heated to 80° C. for 48 hours. Subsequently, the reaction mixture was cooled to room temperature and the volume of the solvent was reduced. The reaction mixture was filtered through a plug of SiO$_2$ applying a ratio diethylether/THF 4:1. After removal of the solvent, the crude product was recrystallized from ethanol. The NMR data were in agreement with values known from literature (Ellis, W. W. et al, Synthesis, structure and properties of chiral titanium and zirconium complexes bearing biaryl strapped substituted cyclopentadienyl ligands, Organometallics (1993), 12(11), 4391-4401).

Yield: 0.086 g (61%).

This yield is higher than the yields obtained in the preparation of the phenylidene bridged bis(indenyl) ligand using processes known so far. For example the yield obtained by Ellis, W. W. et al in Synthesis, structure and properties of chiral titanium and zirconium complexes bearing biaryl strapped substituted cyclopentadienyl ligands, *Organometallics* (1993), 12(11), 4391-4401 was 40% (calculation: 87%× 62%×74%) after three stages. For example, the yield obtained after three stages in EP1059300A1 was 6% (calculation: 49%×53%×23%). For example, the yield obtained by Ijpeij, E. G., et al. in A Suzuki coupling based route to 2,2'-bis(2-indenyl)biphenyl derivatives, *J. Org. Chem.*, 2002, 67, 169 for only the last step was 79%.

1.4 Synthesis of 2,2'-bis(2-indenyl)biphenyl ZrCl$_2$

The synthesis of a zirconium complex from bis(indenyl) ligands is described in EP1059300A1, hereby incorporated by reference. A schematic representation of said synthesis is given in reaction 4 below. The above 2,2'-bis(2-indenyl)biphenyl ligand was deprotonated with n-butyllithium and subsequently reacted with zirconium tetrachloride, ZrCl$_4$, to give targeted bridged metallocene catalyst 2,2'-bis(2-indenyl)biphenyl ZrCl$_2$ (catalyst A).

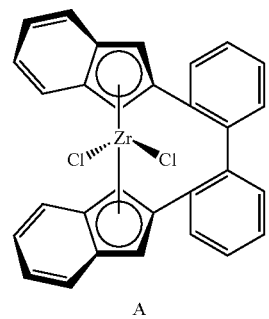

A

2. Procedure for Coupling of 2-indenylboronate and 1,2-dibromobenzene

Similarly, the analogous approach was tested for the synthesis of 1,2-bis(2-indenyl)benzene (see the schematic reaction in reaction 5 below) and gave the desired compound without the formation of homo-coupled side products. The synthesis and results are described below.

(reaction 5)

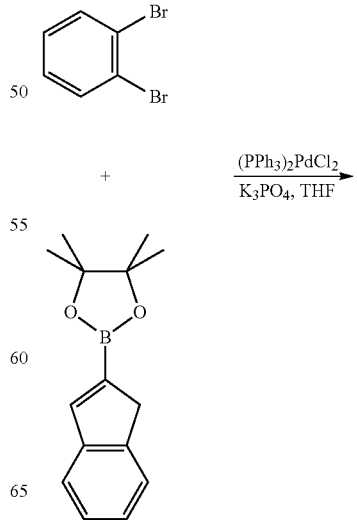

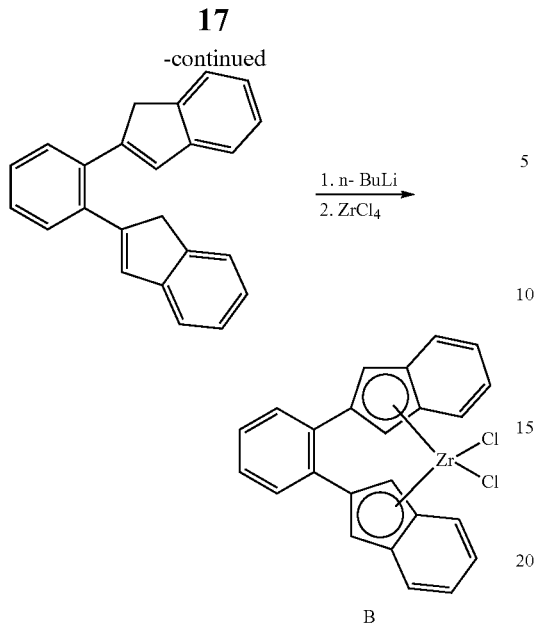
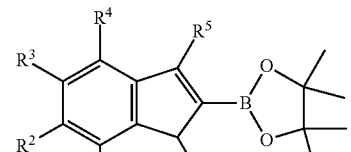

An oven-dried resealable Schlenk tube was charged with (PPh$_3$)$_2$PdCl$_2$ (0.15 g, 0.21 mmol), 2-indenylboronate (2.16 g, 8.93 mmol) and K$_3$PO$_4$ (5.60 g, 26.35 mmol). The Schlenk tube was evacuated and backfilled with argon, and THF (10 ml) and 1,2-dibromobenzene (1.00 g; 4.25 mmol) were added through a rubber septum. The reaction Schlenk tube was sealed and was heated to 80° C. for 20 hours. Subsequently, the reaction mixture was cooled to room temperature and filtered through a plug of SiO$_2$ (It is preferred to use a diethylether/THF 4:1 mixture for washing the product from the column.). GC/MS showed that the reaction was incomplete, so again (PPh$_3$)$_2$PdCl$_2$ (0.15 g, 0.21 mmol) and THF (10 ml) were added.

After 24 hours, GC/MS showed complete conversion. The mixture was concentrated and diethylether was added (final ratio ether/THF 4:1). The mixture was filtered through a plug of SiO$_2$. The filtrate was concentrated and the resulting residue was purified by column chromatography. Yield: 0.98 g (76%). The zirconium complex (catalyst B) was synthesized as in EP1059300A1.

3. Polymerization of Ethylene Using Catalyst A or Catalyst B

Ethylene was homopolymerized using the zirconium complexes (catalyst A or catalyst B) as prepared in the examples as described above. The polymerization conditions were chosen as follows: Al/Zr=2500, 250 ml n-pentane, 10 bar ethylene, 60° C., 1 h. The polymerization activity was determined (kg polyethylene (PE) produced per mol catalyst per hour). The results are given in Table 1 below.

TABLE 1

Ethylene homopolymerization using catalyst A or catalyst B

| Catalyst | catalyst activity (kg PE/mol Cat · h |
|---|---|
| A | 225000 |
| B | 95060 |

The invention claimed is:

1. A process for the preparation of a bridged bis(indenyl) ligand comprising
reacting a 2-indenylpinacolylborane compound of formula (1)

(1)

wherein R$^1$, R$^2$, R$^3$, R$^4$, R$^5$, R$^6$ each independently stand for H, a hydrocarbon radical having 1-20 C-atoms, a halide, an alkoxy group having 1-6 C-atoms, an alkylsulphide, an amine, a Si or B containing group or a P-containing group with a bromosubstituted compound of formula (2)

(Br)$_2$—R (2)

wherein R stands for a bridging group containing at least two sp2-hybridised carbon atoms that are bonded to the indenyl groups at the 2-positions in a solvent in the presence of a Pd catalyst and a base to form the corresponding bridged bis(indenyl) ligand of formula (3)

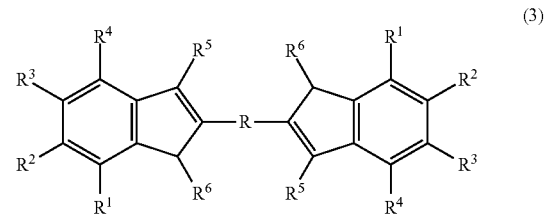

(3)

wherein R and R$^1$, R$^2$, R$^3$, R$^4$, R$^5$ are R$^6$ as described above.

2. The process according to claim 1, wherein the Pd catalyst is bis(triphenylphosphin)palladium dichloride (PPh$_3$)$_2$PdCl$_2$).

3. The process according to claim 1, wherein the base is triethylamine (Et$_3$N).

4. The process according to claim 1, wherein the solvent used is dioxane.

5. The process according to claim 1, wherein R stands for a phenylene or biphenylidene group.

6. The process according to claim 1, wherein R$^1$, R$^2$, R$^3$, R$^4$, R$^5$ and R$^6$ all stand for H.

7. The process according to claim 1, further comprising reacting a 2-bromo indene compound of formula (4)

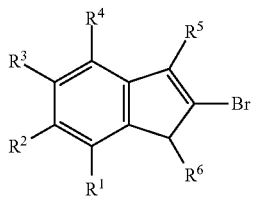
(4)

with pinacolborane of formula (5)

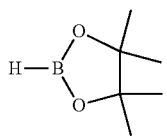
(5)

in a solvent the presence of a Pd catalyst and a base to form the corresponding 2-indenylpinacolylborane compound of formula (1)

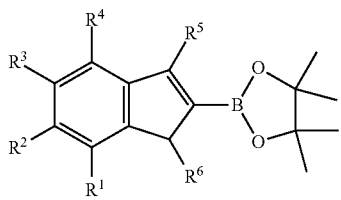
(1)

wherein $R^1$, $R^2$, $R^3$, $R^4$, $R^5$ and $R^6$ are as defined in claim 1.

8. The process according to claim 7, wherein in the preparation of the 2-indenylpinacolylborane compound of formula (1), bis(triphenylphosphin)palladium dichloride ($(PPh_3)_2 PdCl_2$) is used as the Pd catalyst.

9. The process according to claim 7, wherein in the preparation of the 2-indenylpinacolylborane compound of formula (1), $K_3PO_4$ is used as the base.

10. The process according to claim 7, wherein the solvent used in the preparation of the 2-indenylpinacolylborane compound of formula (1) is tetrahydrofuran.

11. The process according to claim 1, further comprising the step of converting the bridged bis(indenyl)ligand of formula (3)

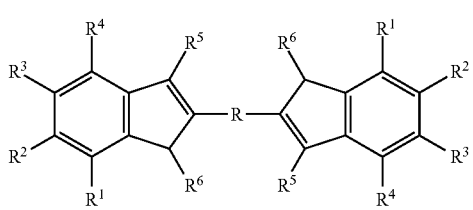
(3)

into the corresponding metallocene complex of formula (6)

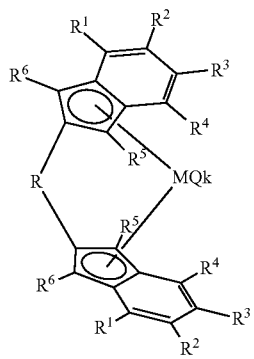
(6)

wherein M stands for a transition metal from the group of lanthanides or from group 3, 4, 5 or 6 of the Periodic System of Elements, wherein Q stands for an anionic ligand to M, wherein k is an integer and stands for the number of anionic ligands, and wherein R, $R^1$, $R^2$, $R^3$, $R^4$, $R^5$ and $R^6$ are as described in claim 1.

12. The process according to claim 11, wherein the bridged bis(indenyl) ligand of formula (3) is converted into its corresponding dianion using an organometallic compound, an amine, a metal hydride, an alkaline earth metal or an alkaline earth metal and the formed dianion is transmetalated with a compound of transition metal M, to form the corresponding metallocene complex of formula (6)

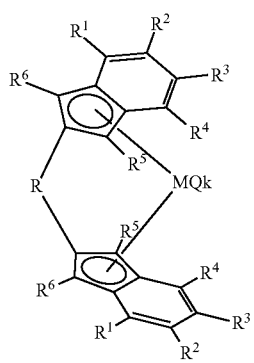
(6)

wherein M stands for a transition metal from the group of lanthanides or from group 3, 4, 5 or 6 of the Periodic System of Elements, wherein Q stands for an anionic ligand to M, wherein k is an integer and stands for the number of anionic ligands, and wherein R, $R^1$, $R^2$, $R^3$, $R^4$, $R^5$ and $R^6$ are as described in claim 1.

* * * * *